United States Patent [19]
Sone

[11] Patent Number: 6,156,886
[45] Date of Patent: Dec. 5, 2000

[54] CYTOCHROME BD TYPE QUINOL OXIDASE GENE OF *BREVIBACTERIUM LACTOFERMENTUM*

[75] Inventor: Nobuhito Sone, Iizuka, Japan

[73] Assignee: Ajinomoto, Co., Inc., Tokyo, Japan

[21] Appl. No.: 09/327,504

[22] Filed: Jun. 8, 1999

[30]     Foreign Application Priority Data

Jun. 11, 1998 [JP] Japan .................................. 10-164019

[51] Int. Cl.$^7$ ......................... C07H 21/04; C12N 15/53; C12N 9/02
[52] U.S. Cl. ....................... 536/23.2; 536/22.1; 536/23.2; 435/6; 435/25; 435/29; 435/252.3; 435/320.1; 435/189
[58] Field of Search ..................... 435/106, 107, 435/252.32, 189, 252.3, 320.1; 536/23.7, 23.1, 23.2

[56]                 References Cited
             U.S. PATENT DOCUMENTS 5,721,284  2/1998  Smits et al. .

FOREIGN PATENT DOCUMENTS

| 0 547 515 A2 | 6/1993 | European Pat. Off. . |
| 0 567 027 A1 | 10/1993 | European Pat. Off. . |
| 0 581 191 A1 | 2/1994 | European Pat. Off. . |
| 0 676 433 A2 | 10/1995 | European Pat. Off. . |
| 0 685 512 A1 | 12/1995 | European Pat. Off. . |
| 0 905 159 A1 | 9/1997 | European Pat. Off. . |
| 195 45 165 A1 | 6/1997 | Germany . |

OTHER PUBLICATIONS

Moshiri et al. Cloning, characterization and expression . . . from *Azotobacter vinelandii*. Journal of Bacteriology vol. 173(19): 6230–6241. Oct. 1991.

Sakamoto et al. Gene structure and quinol oxidase . . . from *Bacillus stearothermophilus*. Biochimica et Biophysica Acta vol. 1411:147–158, 1999.

*Primary Examiner*—Rebecca E. Prouty
*Assistant Examiner*—Manjunath Rao
*Attorney, Agent, or Firm*—Oblon, Spivak, McClelland, Maier & Neustadt, P.C.

[57]                 ABSTRACT

Oligonucleotides are synthesized based on amino acid sequences of the N-terminus of subunit I, and the N-terminus of subunit II of cytochrome bd type quinol oxidase of *Brevibacterium flavum*, PCR is performed by using the oligonucleotides as primers, and chromosome DNA of *B. flavum* as template, and a gene encoding cytochrome bd type quinol oxidase of *B. flavum* is obtained from a chromosome DNA library of *Brevibacterium lactofermentum* using the above obtained amplification fragment as a probe.

13 Claims, 4 Drawing Sheets

```
Br. l cydA   1:  M---DVVDIARWQFGITTVYHFIFVPLTIGLAPLVAIMQTFWQVTGKEHWYRATRFFG  55
B. st cydA   1:  MNGYDPVLLSRILTELTLTVHIIYATIGVGVPLMIAIAQWVGIRKNDMHYILLARRWT  58
E. co cydA   1:  M--LDIVELSRLQFALTAMYHFLFVPLTLGMAFLLAIMETVYVLSGKQIYKDMTKFWG  56
                 *   *    *     *   *b595  * I   **

Br. l cydA  56:  TVLLINFAVGVATGIVQEFQFGMNWSEYSRFVGDVFGGPLALEGLIAFFLESVFLGLWIF  115
B. st cydA  59:  RGFVITVAVGVVTGTAIGLQLSLLWPNFMQLAGQVISLPLFMET-FAFFFEAIFLGIYLY  117
E. co cydA  57:  KLFGINFALGVATGLTMEFQFGTNWSYYSHYVGDIFGAPLAIEGLMAFFLESTFVGLFFF  116
                 *  * ** **       *    *          *   ** * II*** *  *  *

Br. l cydA 116:  GWGKI-PGWLHTASIWIVAIATNISAYFIIVANSFMQHPVGAEYNPETGRAELTDFWALL  174
B. st cydA 118:  TWDRFENQKKHLLLLIPVAIGSSASAHVYYDGERVYEYAAR--FELKNGELVNIDPIVAM  175
E. co cydA 117:  GWDRL-GKVQHMCVTWLVALGSNLSALWILVANGWMQNPIASDFNFETMRMEMVSFSELV  175
                  *         *      **III **

Br. l cydA 175:  TNSTALAAFPHAVAGGFLTAGTFVLGISGWWIIRAHRQAKKAEAEIESKHSMHRPALWVG  234
B. st cydA 174:  FNPAMPTKVAHVLATSYMTSAFVLASIAAWHLWKGNRHIYHRKALHLTMKTAFIFSVASA  235
E. co CYDA 176:  LNPVAQVKFVHTVASGYVTGAMFILGISAWYMLKGRDLAFAKRSFAIAASFGMAAVLSVI  235
                     *     * *   IV*    * *                 V
                               b558

Br. l cydA 235:  WWTTVVSSVALFITGDTQAKLMFVQQPMKMASAESLCETATDPNFSILTIGTHNNCDTV  293
B. st cydA 236:  LVGDL------------SGKFLAEYQPEKLAAAE--WHFETSSHAPLILFGTLEEDNEV  280
E. co cydA 236:  VLGDE------------SGYEMGDVQKTKLAAIEAEWETQPAPAAFTLFGIPDQEEETN  282
                                                   *   * *

Br. L cydA 294:  THLIDVPFVLPFLAEGKFTGVTLQGVNQLQAAAEQAYGPG------------------  333
B. st cydA 281:  KYALEIPYALSILAH-NHPAAVVTGLNDI--PEDERPPL--------------------  316
E. co cydA 283:  KFAIQIPYALGIIAT-RSVDTPVIGLKELMVQHEERIRNGMKAYSLLEQLRSGSTDQAVRDQFNS  346
                   *   *       *

Br. l cydA 334:  ------------------------NYSPNLFVTYWSFRAMIGLMLGSLAIAAI  362
B. st cydA 317:  ---------------------------YIHYL-FDVMWTIGVFLMVVAAV     338
E. co cydA 347:  MKKDLGYGLLLKRYTPNVADATEAQIQQATKDSIPRVAPLYFAFRIMVACG-FLLLAIIA  405
                                                                  *  * *b558   VI Br. l CYDa 363:  AWLLLRKKRTPTGKIARLFQIGSLIAIPFPFLANSAGWIFTEMGRQPWVVHPNPESA  419
B. st cydA 339:  YWLGSIFRWK--WTAKNWFFGLLVAGGPLAMIAIEAGWYLAEVGRQPWILRGYMKTA  393
E. co cydA 406:  LSFWSVIRNR--IGEKKWLLRAALYGIPLPWIAVEAGWFVAEYGRQPWAIGEVLPTA  460
                          *  *  *** *  ****       *
```

*FIG. 2A*

```
Br. l cydA   420: GDARTEMIRMTVDMGVSDHAPWQVWLTLIGFTILYLILFVVWVWLIRRAVLIGPPEEGAP   479
B. st cydA   394: EGATTSAHVDTML-VL-FCLLYIVLVIASATVLIRMFRRNP-VERELEERANRGEVAP   448
E. co cydA   461: VANSSLTAGDLIFSMVLICGLYTLFLVAELFLMFKFARLGPSSLKTGRYHFEQSSTTTQP  520
                             VII Br. l cydA   480: SVEAKTGPATPIGSDMPMTPLQFTVPPQPHVKRNNHGS   517
B. st cydA      :
E. co cydA   521: AR                                     522
```

*FIG. 2B*

```
Br. l cydB  1: M-----DLNTFWFILIAFLFAGYFLLEGFDFGVGILAPIIGKDSAAKNTIIRTIGPV  52
B. st cydB  1: MTLEVIGISVLWLFLFGYIIVASIDFGAGFFSV-YSHWANQQHILHR-IIQRYLSPV  55
E. co cydB  1: MIDYEVL-RFIWWLLVGVLLIGFAVTDGFDMGVGMLTRFLGRNDTERRIMINSIAPH  56
               *     * *         I                 *                *

Br. l cydB  53: WDGNEVWLIVAGGALFAAFPEWYATMFSGMYLPLFLVLVSLIMRVVGLEWRKKVDDPRWQ  112
B. st cydB  56: WEVTNVFLVFFFVGIVGFFPKTAYYYGSILLVPASIAIVLLAIRGSYYAFH-TYGETER-  113
E. co cydB  57: WDGNQVWLITAGGALFAAWPMVYAAAFSGFYVAMILVLASLFFRPVGFDYRSKIEETRWR  116
                *   * *       *         AAAFSGFY II         * *

Br. l cydB  113: KWSDRAIFIGSWTPPLMWGFIFANIFKLACPSRRITPSMLQWLCCAMFNVFAILGALAFTA  173
B. st cydB  114: -NWYLLAYGLTGLFIPASLSIVLTISE-GGFVEENAAGVALDYGKLFASPLSWSVVLLSVT  172
E. co cydB  117: NMWDWGIFIGSFVPPLVIGVAFGNLLQ-GVPFNVDEYLRLYYTGNFFQLLNPFGLLAGVVS  176
                           III                                          IV Br. l cydB  174: LFALHGLAFIRLKTAGRVRTDAAKAAPVVALLAAVTGGPFVLWAAIAYGRSW--------  225
B. st cydB  173: SVLYISAVFLTYYADAAGDEQARALLRRYALLWSGPTMLSALLIIYQLRYHN--------  224
E. co cydB  177: VGMIITQGATYLQMRTVGELHLRTRATAQVAALVTLVCFALAGVWVMYGIDGYVVKSTMD  236
                     V Br. l cydB  226: ---------------------------SWILAVLIIAAVLGGAFALIKDRDGLSFLS  255
B. st cydB  225: ---------------------PEHYDNLWNVAWMLVISFLFFVITVWLLGRQRRFGW  260
E. co cydB  237: HYAASNPLNKEVVREAGAWLVNFNNTPILWAIPALGVVLPLLTILTARMDKAAWAFVF  294
                                                   *         VI Br. L cydB  256: TSVAVIGVVALLFSSLFPNVMPTTLADGVTGYLERLRKPLRIDHPDLDRHCDRTAGCPLP  315
B. st cydB  261: AFIALLFQYAFAFYAYGISHYPYLLYPY--LTIYDGFTNETMAMALIVAFIAGLLLLIP-  317
E. co cydB  295: SSLTLACIILTAGIAMFPFVMPSSTMMNASLTMWDATSSQLTLNVMTWVAVVLVPIILLY  354
                      VII           *                              VIII Br. l cydB  316: RLDLLGVPQTTSRRASVCLKVGKIEY  341
B. st cydB  318: SLYLLMRLFLFNKAYVKGKWEGGKG   342
E. co cydB  355: TAWCYWKMFGRITKEDIERNTHSLY   379
```

*FIG. 3*

SEQUENCE LISTING

```
<160> NUMBER OF SEQ ID NOS: 10

<210> SEQ ID NO 1
<211> LENGTH: 3936
<212> TYPE: DNA
<213> ORGANISM: Brevibacterium lactofermentum
<220> FEATURE:
<221> NAME/KEY: CDS
<222> LOCATION: (933)..(2483)

<400> SEQUENCE: 1
ggatcctctc tgttcaaaac agcacctact cttttactcc cgagttccga cgtgccctcg      60
acgaaagcct agaagtgacg gaccgagatg aggctgctca gaattttaag tttcacgtcc     120
aagacatcat cgaaactggg ttgtttatcg ccagaaataa tggattctgg caaggaaacc     180
tcgtcgttgg cgaaagatat tcccgacgag atgtctgccg aattctcaat tgggaacgaa     240
acaatgagag cacgattat ggttacaaag tggacagcta cacatcgacg tgcccaatct     300
ttgtgaccta tcacaaggct gatgatgtat ccgaagtact cgttaccagg atgaactcgt     360
```

-continued

```
cgatccgaat accettcatt ggtattcccg cggcaaccga aagatcacgt ctaatgagat    420
caagcccatc gctgcgaatg tgtggatctt catgttttg tgaagaagga cgatgccgaa     480
ggccttgatt tcttctacct tggtcaagcg cattcagaaa acagcaaaca gtcatcgatg    540
cccggaaaca aggagttgt gcaaccggtg gtcacaatgg atctacagtt cgacacaccc     600
gtcgaacaaa gcctgtttga gtacctgagc acaaatctcg ccgtaacgga gtaaccaccg    660
caaccaagcg tcgaaaagca aaatcttttc gagtttttgg tgacttgtca acaagggggg    720
agcaaaatca gtcattgaca gggaaaggtt gaccacaatc ggggttagcc tttctaaagt    780
taagctgtga gcgggaactt aggaataaac ttcaacgaca accttaaga  agctcttatt    840 ggttcttcgt tttgtatcga taaatacaat cggtttcctg gctcaataag gctgttcctg    900
tcaatctgta aagaagagga agggaccta gc gtg gat gtc gtt gac atc gcg       953
                                    Val Asp Val Val Asp Ile Ala
                                     1               5 cgg tgg caa ttc gga att acc acc gtc tat cac ttc att ttt gtc cca     1001
Arg Trp Gln Phe Gly Ile Thr Thr Val Tyr His Phe Ile Phe Val Pro
         10              15                  20 ctg acc att ggc tta gca ccg ctg gtc gcg atc atg caa acg ttt tgg    1049
Leu Thr Ile Gly Leu Ala Pro Leu Val Ala Ile Met Gln Thr Phe Trp
     25              30                  35 caa gtt acc ggc aaa gag cac tgg tat cgg gct acg aga ttt ttt ggc    1097
Gln Val Thr Gly Lys Glu His Trp Tyr Arg Ala Thr Arg Phe Phe Gly
 40              45                  50                  55 act gtg ctg ctc atc aac ttc gcg gtt ggt gta gca acg ggc att gtg    1145
Thr Val Leu Leu Ile Asn Phe Ala Val Gly Val Ala Thr Gly Ile Val
                 60                  65                  70 cag gag ttc cag ttc ggt atg aac tgg tcg gaa tat tcg cgt ttc gtc    1193
Gln Glu Phe Gln Phe Gly Met Asn Trp Ser Glu Tyr Ser Arg Phe Val
             75                  80                  85 ggt gat gtt ttc ggc gga ccg ctg gct ttg gag ggg ctc atc gcg ttc    1241
Gly Asp Val Phe Gly Gly Pro Leu Ala Leu Glu Gly Leu Ile Ala Phe
         90                  95                 100 ttc ctt gag tct gtg ttc tta ggt ctg tgg att ttc gga tgg ggg aag    1289
Phe Leu Glu Ser Val Phe Leu Gly Leu Trp Ile Phe Gly Trp Gly Lys
     105                 110                 115 att cct gga tgg ctg cat act gcg tcc att tgg atc gtt gct att gcg    1337
Ile Pro Gly Trp Leu His Thr Ala Ser Ile Trp Ile Val Ala Ile Ala
120                 125                 130                 135 acg aat att tct gcc tat ttc atc atc gtg gcc aac tcg ttt atg cag    1385
Thr Asn Ile Ser Ala Tyr Phe Ile Ile Val Ala Asn Ser Phe Met Gln
             140                 145                 150 cat ccg gtg ggt gct gag tat aac cct gag act ggt cgg gcg gag ctt    1433
His Pro Val Gly Ala Glu Tyr Asn Pro Glu Thr Gly Arg Ala Glu Leu
             155                 160                 165 act gat ttc tgg gct ctt ctc aca aac tcc acc gcg ctg gct gcg ttc    1481
Thr Asp Phe Trp Ala Leu Leu Thr Asn Ser Thr Ala Leu Ala Ala Phe
         170                 175                 180 ccg cat gct gtt gcc ggt ggt ttt tta aca gct gga act ttc gtc ctc    1529
Pro His Ala Val Ala Gly Gly Phe Leu Thr Ala Gly Thr Phe Val Leu
     185                 190                 195 gga att tcg ggt tgg tgg att att cgt gcg cac cgc cag gcg aag aag    1577
Gly Ile Ser Gly Trp Trp Ile Ile Arg Ala His Arg Gln Ala Lys Lys
200                 205                 210                 215 gct gag gcg gaa atc gag tcg aag cat tca atg cac agg ccg gcg ttg    1625
Ala Glu Ala Glu Ile Glu Ser Lys His Ser Met His Arg Pro Ala Leu
                 220                 225                 230 tgg gtt ggt tgg tgg acc aca gtt gtc tct tcc gtg gca ctg ttc atc    1673
```

-continued

```
Trp Val Gly Trp Trp Thr Thr Val Val Ser Ser Val Ala Leu Phe Ile
            235                 240                 245 act ggc gat aca cag gcg aag ctc atg ttc gtg cag cag ccg atg aag    1721
Thr Gly Asp Thr Gln Ala Lys Leu Met Phe Val Gln Gln Pro Met Lys
            250                 255                 260 atg gcg tcg gcg gaa tcc ttg tgt gaa acc gcc aca gat cca aac ttc    1769
Met Ala Ser Ala Glu Ser Leu Cys Glu Thr Ala Thr Asp Pro Asn Phe
        265                 270                 275 tcc att ctg aca att ggt acg cac aac aac tgc gat acg gta acc cac    1817
Ser Ile Leu Thr Ile Gly Thr His Asn Asn Cys Asp Thr Val Thr His
280                 285                 290                 295 ctg atc gat gtt ccg ttt gtg ctt cca ttc ttg gct gaa gga aaa ttc    1865
Leu Ile Asp Val Pro Phe Val Leu Pro Phe Leu Ala Glu Gly Lys Phe
                300                 305                 310 acc ggt gtg act ttg cag ggt gta aac cag ctc caa gct gca gcg gag    1913
Thr Gly Val Thr Leu Gln Gly Val Asn Gln Leu Gln Ala Ala Ala Glu
            315                 320                 325 caa gca tac ggt cct ggc aac tac tcc cct aac ttg ttt gtc acc tac    1961
Gln Ala Tyr Gly Pro Gly Asn Tyr Ser Pro Asn Leu Phe Val Thr Tyr
        330                 335                 340 tgg tca ttc cgc gca atg atc ggc cta atg ctt ggt tct ttg gct atc    2009
Trp Ser Phe Arg Ala Met Ile Gly Leu Met Leu Gly Ser Leu Ala Ile
    345                 350                 355 gct gcg att gcg tgg ctg ttg ctg cgt aag aag cgc aca cca act gga    2057
Ala Ala Ile Ala Trp Leu Leu Leu Arg Lys Lys Arg Thr Pro Thr Gly
360                 365                 370                 375 aag att gct cgt ctc ttc caa atc ggc agc ctc att gcc att cca ttc    2105
Lys Ile Ala Arg Leu Phe Gln Ile Gly Ser Leu Ile Ala Ile Pro Phe
                380                 385                 390 cca ttc ttg gct aac tct gct ggt tgg atc ttc acc gag atg ggc cgc    2153
Pro Phe Leu Ala Asn Ser Ala Gly Trp Ile Phe Thr Glu Met Gly Arg
            395                 400                 405 cag cct tgg gtg gta cac ccg aat cct gaa tct gcc ggc gat gcc cga    2201
Gln Pro Trp Val Val His Pro Asn Pro Glu Ser Ala Gly Asp Ala Arg
        410                 415                 420 aca gag atg atc cgg atg act gtt gat atg ggt gtg tct gat cat gcg    2249
Thr Glu Met Ile Arg Met Thr Val Asp Met Gly Val Ser Asp His Ala
    425                 430                 435 ccg tgg caa gtc tgg ctg act cta att ggc ttc acg att ctc tat ctc    2297
Pro Trp Gln Val Trp Leu Thr Leu Ile Gly Phe Thr Ile Leu Tyr Leu
440                 445                 450                 455 atc ttg ttc gtg gtg tgg gtg tgg ctg att cgc cgc gca gtt ctg atc    2345
Ile Leu Phe Val Val Trp Val Trp Leu Ile Arg Arg Ala Val Leu Ile
                460                 465                 470 gga cca cca gag gaa ggc gct cca tcc gtg gag gca aag act gga ccg    2393
Gly Pro Pro Glu Glu Gly Ala Pro Ser Val Glu Ala Lys Thr Gly Pro
            475                 480                 485 gca acc ccg att ggt tca gat atg ccc atg aca ccg ctg caa ttt acc    2441
Ala Thr Pro Ile Gly Ser Asp Met Pro Met Thr Pro Leu Gln Phe Thr
        490                 495                 500 gtg ccg ccc caa cca cac gtg aaa agg aat aac cat gga tct              2483
Val Pro Pro Gln Pro His Val Lys Arg Asn Asn His Gly Ser
    505                 510                 515 taatacccttt tggtttattc tcatcgcatt tttgtttgcg ggatactttc tcctcgaagg   2543
attcgacttc ggtgtcggaa ttttagcgcc gatcatcggt aaagattccg ccgctaaaaa   2603
cacgatcatc cgcaccatcg gccctgtctg gacggaaat gaagtgtggc tgatcgtggc    2663
aggtggcgct tgtttgctg cattccctga gtggtacgca acgatgttct ccggaatgta    2723
```

-continued

```
tctgccgctg ttcctcgtgc ttgtgtcgtt gatcatgcgc gtggtgggcc ttaatggcg      2783 caagaaagtc gatgatcctc gttggcaaaa gtggtctgac cgggccatct ttattggttc      2843
ttggactcca ccgctgatgt ggggattcat cttcgccaat attttcaagc ttgcatgccc      2903
atcaaggcgg atcacaccat cgatgctgca gtggctctgc tgtgcaatgt caacgtctt      2963 cgccatcctg ggtgcacttg cattcactgc gctgttcgct cttcatggcc ttgcattcat      3023
ccgcctgaaa actgctggtc gggtgcgcac cgatgcggcg aaggcagctc cagtagtcgc      3083
acttcttgct gcggtgactg gtggacctt cgtgttgtgg gctgccatcg catacggccg      3143
ttcctggtcc tggatcctcg cagtgctgat catcgcagcg gttctcggtg gagctttcgc      3203
actgatcaaa gaccgcgatg gattaagctt cctgtccact tccgtcgctg tcatcggtgt      3263
agttgcactg ctgtttagtt ccctattccc caacgtcatg ccaacaacgc ttgccgatgg      3323
cgtgactgga tatttggaac gcctccgcaa gccactacgc attgaccatc ctgacttgga      3383
ccgccactgt gatcgcaccg ctggttgtcc tctaccaagg ctggacctac tgggtgttcc      3443
gcaaacgact tcacgccgag ccagtgtctg cctaaaagtt ggaaaaattg agtactaaat      3503
ctgacgctcc ggctagtcgc cgcacaggcc ccgtcgatcc gcggcttttg cgcctatccc      3563
ctgctacccg ccgttgggtg ataatcgcag gtgttctcac cgcgttgaaa actctcgcga      3623
cagtcgcaat gggcttgctc atcggccaga tggcagcggg catcattgag gtttcgggaa      3683
gttctttgcc ccgaatggaa ctcatcgcgc tcgccatcac ggtggttgtg cgcggacttc      3743
ttgcgtgggc acaggatcgg ttcggagcgc gcatcgtccc aggtgactgt ggatcttcgg      3803
gagaaaaccc tgcggcacct ggcacaaagc gatccccgca ccatcgatca agccttgtgg      3863
cgcacccgtt tgacctctgg ccttgatggt ttggggcctt acctcaccgg attttgccg      3923 cactggccgc cac                                                         3936
```

<210> SEQ ID NO 2
<211> LENGTH: 517
<212> TYPE: PRT
<213> ORGANISM: Brevibacterium lactofermentum

<400> SEQUENCE: 2

Val Asp Val Val Asp Ile Ala Arg Trp Gln Phe Gly Ile Thr Thr Val
 1               5                  10                  15

Tyr His Phe Ile Phe Val Pro Leu Thr Ile Gly Leu Ala Pro Leu Val
                20                  25                  30

Ala Ile Met Gln Thr Phe Trp Gln Val Thr Gly Lys Glu His Trp Tyr
            35                  40                  45

Arg Ala Thr Arg Phe Phe Gly Thr Val Leu Leu Ile Asn Phe Ala Val
        50                  55                  60

Gly Val Ala Thr Gly Ile Val Gln Glu Phe Gln Phe Gly Met Asn Trp
65                  70                  75                  80

Ser Glu Tyr Ser Arg Phe Val Gly Asp Val Phe Gly Gly Pro Leu Ala
                85                  90                  95

Leu Glu Gly Leu Ile Ala Phe Leu Glu Ser Val Phe Leu Gly Leu
                100                 105                 110

Trp Ile Phe Gly Trp Gly Lys Ile Pro Gly Trp Leu His Thr Ala Ser
            115                 120                 125

Ile Trp Ile Val Ala Ile Ala Thr Asn Ile Ser Ala Tyr Phe Ile Ile
        130                 135                 140

Val Ala Asn Ser Phe Met Gln His Pro Val Gly Ala Glu Tyr Asn Pro
145                 150                 155                 160

-continued

```
Glu Thr Gly Arg Ala Glu Leu Thr Asp Phe Trp Ala Leu Leu Thr Asn
                165                 170                 175
Ser Thr Ala Leu Ala Ala Phe Pro His Ala Val Ala Gly Gly Phe Leu
            180                 185                 190
Thr Ala Gly Thr Phe Val Leu Gly Ile Ser Gly Trp Trp Ile Ile Arg
        195                 200                 205
Ala His Arg Gln Ala Lys Lys Ala Glu Ala Glu Ile Glu Ser Lys His
    210                 215                 220
Ser Met His Arg Pro Ala Leu Trp Val Gly Trp Thr Thr Val Val
225                 230                 235                 240
Ser Ser Val Ala Leu Phe Ile Thr Gly Asp Thr Gln Ala Lys Leu Met
                245                 250                 255
Phe Val Gln Gln Pro Met Lys Met Ala Ser Ala Glu Ser Leu Cys Glu
            260                 265                 270
Thr Ala Thr Asp Pro Asn Phe Ser Ile Leu Thr Ile Gly Thr His Asn
        275                 280                 285
Asn Cys Asp Thr Val Thr His Leu Ile Asp Val Pro Phe Val Leu Pro
    290                 295                 300
Phe Leu Ala Glu Gly Lys Phe Thr Gly Val Thr Leu Gln Gly Val Asn
305                 310                 315                 320
Gln Leu Gln Ala Ala Ala Glu Gln Ala Tyr Gly Pro Gly Asn Tyr Ser
                325                 330                 335
Pro Asn Leu Phe Val Thr Tyr Trp Ser Phe Arg Ala Met Ile Gly Leu
            340                 345                 350
Met Leu Gly Ser Leu Ala Ile Ala Ala Ile Ala Trp Leu Leu Leu Arg
        355                 360                 365
Lys Lys Arg Thr Pro Thr Gly Lys Ile Ala Arg Leu Phe Gln Ile Gly
    370                 375                 380
Ser Leu Ile Ala Ile Pro Phe Pro Phe Leu Ala Asn Ser Ala Gly Trp
385                 390                 395                 400
Ile Phe Thr Glu Met Gly Arg Gln Pro Trp Val Val His Pro Asn Pro
                405                 410                 415
Glu Ser Ala Gly Asp Ala Arg Thr Glu Met Ile Arg Met Thr Val Asp
            420                 425                 430
Met Gly Val Ser Asp His Ala Pro Trp Gln Val Trp Leu Thr Leu Ile
        435                 440                 445
Gly Phe Thr Ile Leu Tyr Leu Ile Leu Phe Val Val Trp Val Trp Leu
    450                 455                 460
Ile Arg Arg Ala Val Leu Ile Gly Pro Pro Glu Glu Gly Ala Pro Ser
465                 470                 475                 480
Val Glu Ala Lys Thr Gly Pro Ala Thr Pro Ile Gly Ser Asp Met Pro
                485                 490                 495
Met Thr Pro Leu Gln Phe Thr Val Pro Pro Gln Pro His Val Lys Arg
            500                 505                 510
Asn Asn His Gly Ser
            515

<210> SEQ ID NO 3
<211> LENGTH: 3936
<212> TYPE: DNA
<213> ORGANISM: Brevibacterium lactofermentum
<220> FEATURE:
<221> NAME/KEY: CDS
<222> LOCATION: (2476)..(3498)
```

```
<400> SEQUENCE: 3
ggatcctctc tgttcaaaac agcacctact cttttactcc cgagttccga cgtgccctcg         0
acgaaagcct agaagtgacg gaccgagatg aggctgctca gaattttaag tttcacgtcc        20
aagacatcat cgaaactggg ttgtttatcg ccagaaataa tggattctgg caaggaaacc        80
tcgtcgttgg cgaaagatat tcccgacgag atgtctgccg aattctcaat gggaacgaa        840
acaatgagag cacgatttat ggttacaaag tggacagcta cacatcgacg tgcccaatct       300
ttgtgaccta tcacaaggct gatgatgtat ccgaagtact cgttaccagg atgaactcgt       360
cgatccgaat acccttcatt ggtattcccg cggcaaccga aagatcacgt ctaatgagat       420
caagcccatc gctgcgaatg tgtggatctt catgtttttg tgaagaagga cgatgccgaa       480
ggccttgatt tcttctacct tggtcaagcg cattcagaaa acagcaaaca gtcatcgatg       540
cccggaaaca aaggagttgt gcaaccggtg gtcacaatgg atctacagtt cgacacaccc       600
gtcgaacaaa gcctgtttga gtacctgagc acaaatctcg ccgtaacgga gtaaccaccg       660
caaccaagcg tcgaaaagca aaatcttttc gagtttttgg tgacttgtca acaaggggg       720
agcaaaatca gtcattgaca gggaaaggtt gaccacaatc ggggttagcc tttctaaagt       780
taagctgtga gcgggaactt aggaataaac ttcaacgaca acctttaaga agctcttatt       840
ggttcttcgt tttgtatcga taaatacaat cggtttcctg gctcaataag gctgttcctg       900
tcaatctgta aagaagagga aggggaccta gcgtggatgt cgttgacatc gcgcggtggc       960
aattcggaat taccaccgtc tatcacttca ttttgtccc actgaccatt ggcttagcac      1020
cgctggtcgc gatcatgcaa acgttttggc aagttaccgg caaagagcac tggtatcggg      1080
ctacgagatt ttttggcact gtgctgctca tcaacttcgc ggttggtgta gcaacgggca      1140
ttgtgcagga gttccagttc ggtatgaact ggtcggaata ttcgcgtttc gtcggtgatg      1200
ttttcggcgg accgctggct ttggagggc tcatcgcgtt cttccttgag tctgtgttct      1260
taggtctgtg gattttcgga tggggaaga ttcctggatg gctgcatact gcgtccattt      1320
ggatcgttgc tattgcgacg aatatttctg cctatttcat catcgtggcc aactcgttta      1380
tgcagcatcc ggtgggtgct gagtataacc ctgagactgg tcgggcggag cttactgatt      1440
tctgggctct tctcacaaac tccaccgcgc tggctgcgtt cccgcatgct gttgccggtg      1500
gttttttaac agctggaact ttcgtcctcg gaatttcggg ttggtggatt attcgtgcgc      1560
accgccaggc gaagaaggct gaggcggaaa tcgagtcgaa gcattcaatg cacaggccgg      1620
cgttgtgggt tggttggtgg accacagttg tctcttccgt ggcactgttc atcactggcg      1680
atacacaggc gaagctcatg ttcgtgcagc agccgatgaa gatggcgtcg gcggaatcct      1740
tgtgtgaaac cgccacagat ccaaacttct ccattctgac aattggtacg cacaacaact      1800
gcgatacggt aacccacctg atcgatgttc cgtttgtgct tccattcttg gctgaaggaa      1860
aattcaccgg tgtgactttg cagggtgtaa accagctcca agctgcagcg gagcaagcat      1920
acggtcctgg caactactcc cctaacttgt ttgtcaccta ctggtcattc cgcgcaatga      1980
tcggcctaat gcttggttct ttggctatcg ctgcgattgc gtgctgttg ctgcgtaaga      2040
agcgcacacc aactgaaaag attgctcgtc tcttccaaat cggcagcctc attgccattc      2100
cattcccatt cttggctaac tctgctggtt ggatcttcac cgagatgggc cgccagcctt      2160
gggtggtaca cccgaatcct gaatctgccg gcgatgcccg aacagagatg atccggatga      2220
ctgttgatat gggtgtgtct gatcatgcgc cgtggcaagt ctggctgact ctaattggct      2280
tcacgattct ctatctcatc ttgttcgtgg tgtgggtgtg gctgattcgc cgcgcagttc      2340
```

-continued

```
tgatcggacc accagaggaa ggcgctccat ccgtggaggc aaagactgga ccggcaaccc    2400
cgattggttc agatatgccc atgacaccgc tgcaatttac cgtgccgccc aaccacacg     2460 tgaaaggaa taacc atg gat ctt aat acc ttt tgg ttt att ctc atc gca      2511
           Met Asp Leu Asn Thr Phe Trp Phe Ile Leu Ile Ala
            1               5                   10 ttt ttg ttt gcg gga tac ttt ctc ctc gaa gga ttc gac ttc ggt gtc      2559
Phe Leu Phe Ala Gly Tyr Phe Leu Leu Glu Gly Phe Asp Phe Gly Val
             15                  20                  25 gga att tta gcg ccg atc atc ggt aaa gat tcc gcc gct aaa aac acg      2607
Gly Ile Leu Ala Pro Ile Ile Gly Lys Asp Ser Ala Ala Lys Asn Thr
         30                  35                  40 atc atc cgc acc atc ggc cct gtc tgg gac gga aat gaa gtg tgg ctg      2655
Ile Ile Arg Thr Ile Gly Pro Val Trp Asp Gly Asn Glu Val Trp Leu
 45                  50                  55                  60 atc gtg gca ggt ggc gct ttg ttt gct gca ttc cct gag tgg tac gca      2703
Ile Val Ala Gly Gly Ala Leu Phe Ala Ala Phe Pro Glu Trp Tyr Ala
                 65                  70                  75 acg atg ttc tcc gga atg tat ctg ccg ctg ttc ctc gtg ctt gtg tcg      2751
Thr Met Phe Ser Gly Met Tyr Leu Pro Leu Phe Leu Val Leu Val Ser
             80                  85                  90 ttg atc atg cgc gtg gtg ggc ctt gaa tgg cgc aag aaa gtc gat gat      2799
Leu Ile Met Arg Val Val Gly Leu Glu Trp Arg Lys Lys Val Asp Asp
         95                  100                 105 cct cgt tgg caa aag tgg tct gac cgg gcc atc ttt att ggt tct tgg      2847
Pro Arg Trp Gln Lys Trp Ser Asp Arg Ala Ile Phe Ile Gly Ser Trp
 110                 115                 120 act cca ccg ctg atg tgg gga ttc atc ttc gcc aat att ttc aag ctt      2895
Thr Pro Pro Leu Met Trp Gly Phe Ile Phe Ala Asn Ile Phe Lys Leu
125                 130                 135                 140 gca tgc cca tca agg cgg atc aca cca tcg atg ctg cag tgg ctc tgc      2943
Ala Cys Pro Ser Arg Arg Ile Thr Pro Ser Met Leu Gln Trp Leu Cys
                 145                 150                 155 tgt gca atg ttc aac gtc ttc gcc atc ctg ggt gca ctt gca ttc act      2991
Cys Ala Met Phe Asn Val Phe Ala Ile Leu Gly Ala Leu Ala Phe Thr
             160                 165                 170 gcg ctg ttc gct ctt cat ggc ctt gca ttc atc cgc ctg aaa act gct      3039
Ala Leu Phe Ala Leu His Gly Leu Ala Phe Ile Arg Leu Lys Thr Ala
         175                 180                 185 ggt cgg gtg cgc acc gat gcg gcg aag gca gct cca gta gtc gca ctt      3087
Gly Arg Val Arg Thr Asp Ala Ala Lys Ala Ala Pro Val Val Ala Leu
     190                 195                 200 ctt gct gcg gtg act ggt gga cct ttc gtg ttg tgg gct gcc atc gca      3135
Leu Ala Ala Val Thr Gly Gly Pro Phe Val Leu Trp Ala Ala Ile Ala
205                 210                 215                 220 tac ggc cgt tcc tgg tcc tgg atc ctc gca gtg ctg atc atc gca gcg      3183
Tyr Gly Arg Ser Trp Ser Trp Ile Leu Ala Val Leu Ile Ile Ala Ala
                 225                 230                 235 gtt ctc ggt gga gct ttc gca ctg atc aaa gac cgc gat gga tta agc      3231
Val Leu Gly Gly Ala Phe Ala Leu Ile Lys Asp Arg Asp Gly Leu Ser
             240                 245                 250 ttc ctg tcc act tcc gtc gct gtc atc ggt gta gtt gca ctg ctg ttt      3279
Phe Leu Ser Thr Ser Val Ala Val Ile Gly Val Val Ala Leu Leu Phe
         255                 260                 265 agt tcc cta ttc ccc aac gtc atg cca aca acg ctt gcc gat ggc gtg      3327
Ser Ser Leu Phe Pro Asn Val Met Pro Thr Thr Leu Ala Asp Gly Val
     270                 275                 280 act gga tat ttg gaa cgc ctc cgc aag cca cta cgc att gac cat cct      3375
Thr Gly Tyr Leu Glu Arg Leu Arg Lys Pro Leu Arg Ile Asp His Pro
```

|  |  |  |  |  |  |  |  |  |  |  |
|---|---|---|---|---|---|---|---|---|---|---|
| 285 |  |  |  | 290 |  |  | 295 |  |  | 300 |

```
gac ttg gac cgc cac tgt gat cgc acc gct ggt tgt cct cta cca agg    3423
Asp Leu Asp Arg His Cys Asp Arg Thr Ala Gly Cys Pro Leu Pro Arg
                305                 310                 315 ctg gac cta ctg ggt gtt ccg caa acg act tca cgc cga gcc agt gtc    3471
Leu Asp Leu Leu Gly Val Pro Gln Thr Thr Ser Arg Arg Ala Ser Val
320                 325                 330 tgc cta aaa gtt gga aaa att gag tac taaatctgac gctccggcta          3518
Cys Leu Lys Val Gly Lys Ile Glu Tyr
        335                 340 gtcgccgcac aggccccgtc gatccgcggc ttttgcgcct atccctgct accgccgtt    3578 gggtgataat cgcaggtgtt ctcaccgcgt tgaaaactct cgcgacagtc gcaatgggct  3638
tgctcatcgg ccagatggca gcgggcatca ttgaggtttc gggaagttct ttgccccgaa  3698
tggaactcat cgcgctcgcc atcacggtgg ttgtgcgcgg acttcttgcg tgggcacagg  3758
atcggttcgg agcgcgcatc gtcccaggtg actgtggatc ttcgggagaa aaccctgcgg  3818
cacctggcac aaagcgatcc ccgcaccatc gatcaagcct tgtggcgcac ccgtttgacc  3878
tctggccttg atggtttggg gccttacctc accggatttt tgccgcactg gccgccac    3936
```

<210> SEQ ID NO 4
<211> LENGTH: 341
<212> TYPE: PRT
<213> ORGANISM: Brevibacterium lactofermentum

<400> SEQUENCE: 4

```
Met Asp Leu Asn Thr Phe Trp Phe Ile Leu Ile Ala Phe Leu Phe Ala
 1               5                  10                  15

Gly Tyr Phe Leu Leu Glu Gly Phe Asp Phe Gly Val Gly Ile Leu Ala
                20                  25                  30

Pro Ile Ile Gly Lys Asp Ser Ala Ala Lys Asn Thr Ile Ile Arg Thr
            35                  40                  45

Ile Gly Pro Val Trp Asp Gly Asn Glu Val Trp Leu Ile Val Ala Gly
        50                  55                  60

Gly Ala Leu Phe Ala Ala Phe Pro Glu Trp Tyr Ala Thr Met Phe Ser
65                  70                  75                  80

Gly Met Tyr Leu Pro Leu Phe Leu Val Leu Val Ser Leu Ile Met Arg
                85                  90                  95

Val Val Gly Leu Glu Trp Arg Lys Lys Val Asp Asp Pro Arg Trp Gln
            100                 105                 110

Lys Trp Ser Asp Arg Ala Ile Phe Ile Gly Ser Trp Thr Pro Pro Leu
        115                 120                 125

Met Trp Gly Phe Ile Phe Ala Asn Ile Phe Lys Leu Ala Cys Pro Ser
130                 135                 140

Arg Arg Ile Thr Pro Ser Met Leu Gln Trp Leu Cys Cys Ala Met Phe
145                 150                 155                 160

Asn Val Phe Ala Ile Leu Gly Ala Leu Ala Phe Thr Ala Leu Phe Ala
                165                 170                 175

Leu His Gly Leu Ala Phe Ile Arg Leu Lys Thr Ala Gly Arg Val Arg
            180                 185                 190

Thr Asp Ala Ala Lys Ala Ala Pro Val Val Ala Leu Leu Ala Ala Val
        195                 200                 205

Thr Gly Gly Pro Phe Val Leu Trp Ala Ala Ile Ala Tyr Gly Arg Ser
    210                 215                 220

Trp Ser Trp Ile Leu Ala Val Leu Ile Ile Ala Ala Val Leu Gly Gly
```

```
                225                 230                 235                 240
Ala Phe Ala Leu Ile Lys Asp Arg Asp Gly Leu Ser Phe Leu Ser Thr
                    245                 250                 255

Ser Val Ala Val Ile Gly Val Val Ala Leu Leu Phe Ser Ser Leu Phe
                260                 265                 270

Pro Asn Val Met Pro Thr Thr Leu Ala Asp Gly Val Thr Gly Tyr Leu
                275                 280                 285

Glu Arg Leu Arg Lys Pro Leu Arg Ile Asp His Pro Asp Leu Asp Arg
    290                 295                 300

His Cys Asp Arg Thr Ala Gly Cys Pro Leu Pro Arg Leu Asp Leu Leu
305                 310                 315                 320

Gly Val Pro Gln Thr Thr Ser Arg Arg Ala Ser Val Cys Leu Lys Val
                    325                 330                 335

Gly Lys Ile Glu Tyr
            340
```

<210> SEQ ID NO 5
<211> LENGTH: 19
<212> TYPE: PRT
<213> ORGANISM: Brevibacterium lactofermentum
<220> FEATURE:
<221> NAME/KEY: UNSURE
<222> LOCATION: (18)

<400> SEQUENCE: 5

```
Met Asp Val Val Asp Ile Ala Arg Trp Gln Phe Gly Ile Thr Ala Val
 1               5                  10                  15

Tyr Xaa Phe
```

.<210> SEQ ID NO 6
<211> LENGTH: 20
<212> TYPE: PRT
<213> ORGANISM: Brevibacterium lactofermentum
<220> FEATURE:
<221> NAME/KEY: UNSURE
<222> LOCATION: (16,17)

<400> SEQUENCE: 6

```
Met Asp Leu Asn Thr Phe Trp Phe Ile Leu Ile Ala Phe Leu Phe Xaa
 1               5                  10                  15

Xaa Tyr Phe Leu
            20
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer for
      PCR
<220> FEATURE:
<221> NAME/KEY: misc_feature
<222> LOCATION: (9,12)
<223> OTHER INFORMATION: n=a or c or g or t

<400> SEQUENCE: 7
atggaygtng tngayatygc                                                  20

<210> SEQ ID NO 8
<211> LENGTH: 20
<212> TYPE: DNA
<213> ORGANISM: Artificial Sequence
<220> FEATURE:

```
<223> OTHER INFORMATION: Description of Artificial Sequence: primer for
      PCR

<400> SEQUENCE: 8
caraargtrt tvarrtccat                                                    20

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: primer for
      PCR

<400> SEQUENCE: 9
cgccagggtt ttcccagtca cgac                                               24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: primer for
      PCR

<400> SEQUENCE: 10
gagcggataa caatttcaca cagg                                               24
```

CYTOCHROME BD TYPE QUINOL OXIDASE GENE OF *BREVIBACTERIUM LACTOFERMENTUM*

TECHNICAL FIELD

The present invention relates to a cytochrome bd type quinol oxidase of *Brevibacterium lactofermentum* and a DNA encoding the same.

BACKGROUND ART

Most of organisms acquire energy necessary for life activity by respiration. In higher organisms, carbohydrates, proteins, and aliphatic acids are degraded into acetyl-CoA by the glycolytic pathway and the β-oxidation in cytoplasm, and acetyl-CoA is degraded by the citric acid cycle in mitochondria. The resulting energy is saved as reducing power of NADH and $FADH_2$. Finally, NADH is completely oxidized to water by the subsequent electron transport system that is present on mitochondrial inner membranes, and a proton concentration gradient is formed in a coupled manner to the oxidation, and serves as driving force of the ATP synthesis.

Since the bacterial respiratory chain generally comprises various functional enzyme complexes depending on species and growing circumstance, the energy conservation efficiency may vary to a great extent. For example, *Escherichia coli* contains at least two kinds of quinol oxidase, bo type and bd type, which function as terminal oxidases in the respiratory chain. When a wild-type strain carrying the enzymes of the both types, a mutant strain carrying only the bo type, and a mutant strain carrying only the bd type are compared as for growth yield observed in aerobic culture, the growth yield is the lowest in the mutant carrying only the bd type enzyme, and depends on the kind of the terminal oxidases and their energy conservation efficiency (Lecture Abstract for The Conference of The Society for Bioscience and Bioengineering, Japan, 1995, Subject No. 357).

Coryneform bacteria such as *Brevibacterium lactofermentum* and *Brevibacterium flavum* are gram-positive and aerobic bacteria that are industrially utilized for amino acid producers. Although terminal oxidases of the respiratory chain have been well investigated as for those of Proteobacteria, which is phylogenetically quite far from the coryneform bacteria, and those of *Bacillus subtilis* and the thermophilic Bacillus, which are also gram-positive bacteria like the coryneform bacteria but phylogenetically somewhat different from them, the electron transport system of respiratory chain in coryneform bacteria has not been investigated in detail. It is considered that it is important to elucidate the electron transport system of the respiratory chain, which is the key of the energy metabolism, in coryneform bacteria in view of collecting fundamental data for improving productivity of useful substances. Further, if enzymes involved in the electron transport system of the respiratory chain in coryneform bacteria and genes therefor are identified, they may be useful for, for example, creating strains with higher energy efficiency.

To date, it has been reported that the respiration of *Brevibacterium lactofermentum* is coupled to the proton transport, and it involves cytochromes a, b, and c (Kawahara, Y., et al. (1988) *Agric. Biol. Chem.*, 52(8), 1979–1983). Cytochrome bd type quinol oxidase of *Brevibacterium flavum* has also been purified and characterized (Kusumoto, Sone and Sakamoto, "Respiratory Chain of Amino Acid Fermenting Bacterium, *Brevibacterium flavum*, and Characteristics of Its Cytochrome bd Type Menaquinol Oxidase", Abstracts of the 23th Symposium of Bioenergy Study Group, 1997). However, there has not been any report concerning the genes encoding cytochrome bd type quinol oxidase of coryneform bacteria.

DESCRIPTION OF THE INVENTION

The present invention has been accomplished from the aforementioned point of view, and its object is to obtain a gene of cytochrome bd type quinol oxidase of coryneform bacteria, and elucidate its structure.

The present inventors synthesized oligonucleotides based on amino acid sequences of the N-terminus of subunit I, and the N-terminus of subunit II of cytochrome bd type quinol oxidase of *Brevibacterium flavum*, and preformed PCR by utilizing the oligonucleotides as primers, and a chromosomal DNA of *Brevibacterium flavum* as template to obtain an amplified fragment. Further, they screened a chromosomal DNA library of wild-type *Brevibacterium lactofermentum* strain by using the amplified fragment as a probe, and successfully obtained a gene encoding a cytochrome bd type quinol oxidase of *Brevibacterium lactofermentum*. Thus, the present invention has been completed.

That is, the present invention provides:

(1) a DNA fragment encoding a polypeptide defined in the following (A) or (B;
  (A) a polypeptide which has an amino acid sequence shown in SEQ ID NO: 2 of Sequence Listing,
  (B) a polypeptide which has an amino acid sequence shown in SEQ ID NO: 2 of Sequence Listing comprising substitution, deletion, insertion, addition or inversion of one or a plurality of amino acid residues in the amino acid sequence, and can constitute a protein exhibiting cytochrome bd type quinol oxidase activity together with a subunit II of cytochrome bd type quinol oxidase having an amino acid sequence shown in SEQ ID NO: 4, (2) a DNA fragment encoding a polypeptide defined in the following (C) or (D);
  (C) a polypeptide which has an amino acid sequence shown in SEQ ID NO: 4 of Sequence Listing,
  (D) a polypeptide which has an amino acid sequence shown in SEQ ID NO: 4 of Sequence Listing comprising substitution, deletion, insertion, addition or inversion of one or a plurality of amino acid residues in the amino acid sequence, and can constitute a protein exhibiting cytochrome bd type quinol oxidase activity together with a subunit I of cytochrome bd type quinol oxidase having an amino acid sequence shown in SEQ ID NO: 2, (3) a DNA fragment encoding a polypeptide defined in the following (A) or (B), and a polypeptide defined in the following (C) or (D);
  (A) a polypeptide which has an amino acid sequence shown in SEQ ID NO: 2 of Sequence Listing,
  (B) a polypeptide which has an amino acid sequence shown in SEQ ID NO: 2 of Sequence Listing comprising substitution, deletion, insertion, addition or inversion of one or a plurality of amino acid residues in the amino acid sequence, and can constitute a protein exhibiting cytochrome bd type quinol oxidase activity together with a subunit II of cytochrome bd type quinol oxidase having an amino acid sequence shown in SEQ ID NO: 4,
  (C) a polypeptide which has an amino acid sequence shown in SEQ ID NO: 4 of Sequence Listing, (D) a polypeptide which has an amino acid sequence shown in SEQ ID NO: 4 of Sequence Listing comprising substitution, deletion, insertion, addition or inversion of one or a plurality of amino acid residues in the amino acid sequence, and can constitute a protein exhibiting cytochrome bd type quinol oxidase activity together with a subunit I of cytochrome bd type quinol oxidase having an amino acid sequence shown in SEQ ID NO: 2, (4) The DNA of above (1), which is a DNA defined in the following (a) or (b):

(a) a DNA having a nucleotide sequence corresponding to nucleotide numbers 933 to 2483 in the nucleotide sequence depicted in SEQ ID NO: 1 in Sequence Listing; or (b) a DNA which is hybridizable with the nucleotide sequence of above (a) under a stringent condition, and which codes for a polypeptide which can constitute a protein exhibiting cytochrome bd type quinol oxidase activity together with a subunit II of cytochrome bd type quinol oxidase having an amino acid sequence shown in SEQ ID NO: 4.

(5) The DNA of about (2), which is a DNA defined in the following (c) or (d):

(c) a DNA having a nucleotide sequence corresponding to nucleotide numbers 2476 to 3498 in the nucleotide sequence depicted in SEQ ID NO: 3 in Sequence Listing; or (d) a DNA which is hybridizable with the nucleotide sequence of above (c) under a stringent condition, and which codes for a polypeptide which can constitute a protein exhibiting cytochrome bd type quinol oxidase activity together with a subunit I of cytochrome bd type quinol oxidase having an amino acid sequence shown in SEQ ID NO: 2.

(6) The DNA of above (3), which comprising a DNA defined in the following (a) or (b), and a DNA defined in the following (c) or (d):

(a) a DNA having a nucleotide sequence corresponding to nucleotide numbers 933 to 2483 in the nucleotide sequence depicted in SEQ ID NO: 1 in Sequence Listing; or (b) a DNA which is hybridizable with the nucleotide sequence of above (a) under a stringent condition, and which codes for a polypeptide which can constitute a protein exhibiting cytochrome bd type quinol oxidase activity together with a subunit II of cytochrome bd type quinol oxidase having an amino acid sequence shown in SEQ ID NO: 4; and (c) a DNA having a nucleotide sequence corresponding to nucleotide numbers 2476 to 3498 in the nucleotide sequence depicted in SEQ ID NO: 3 in Sequence Listing; or (d) a DNA which is hybridizable with the nucleotide sequence of above (c) under a stringent condition, and which codes for a polypeptide which can constitute a protein exhibiting cytochrome bd type quinol oxidase activity together with a subunit I of cytochrome bd type quinol oxidase having an amino acid sequence shown in SEQ ID NO: 2.

(7) A DNA fragment defined in the above (1) which has a nucleotide sequence comprising nucleotides of the nucleotide numbers 933 to 2483 in the nucleotide sequence shown in SEQ ID NO: 1, (8) a DNA fragment defined in the above (2) which has a nucleotide sequence comprising nucleotides of the nucleotide numbers 2476 to 3498 in the nucleotide sequence shown in SEQ ID NO: 1, and (9) a DNA fragment defined in the above (3) which has a nucleotide sequence comprising nucleotides of the nucleotide numbers 933 to 3498 in the nucleotide sequence shown in SEQ ID NO: 1.

In the present description, the term cytochrome bd type quinol oxidase activity means activity exhibiting oxidoreduction differential absorption spectra of cytochrome b and cytochrome d, which is for oxidizing a reduced type quinone compounds (quinols) with consumption of oxygen. A DNA fragment that encodes cytochrome bd type quinol oxidase or a subunit thereof will be referred to as the "DNA of the present invention" as the case may be.

BRIEF DESCRIPTION OF THE DRAWINGS

FIG. 2 represents amino acid sequence alignment of subunits I of cytochrome bd type quinol oxidases of *Brevibacterium lactofermentum, Bacillus stearothermophilus* and *Escherichia coli*.

FIG. 3 represents amino acid sequence alignment of subunits II of cytochrome bd type quinol oxidases of *Brevibacterium lactofermentum, Bacillus stearothermophilus* and *Escherichia coli*.

DETAILED DESCRIPTION OF THE INVENTION

Figure 1:
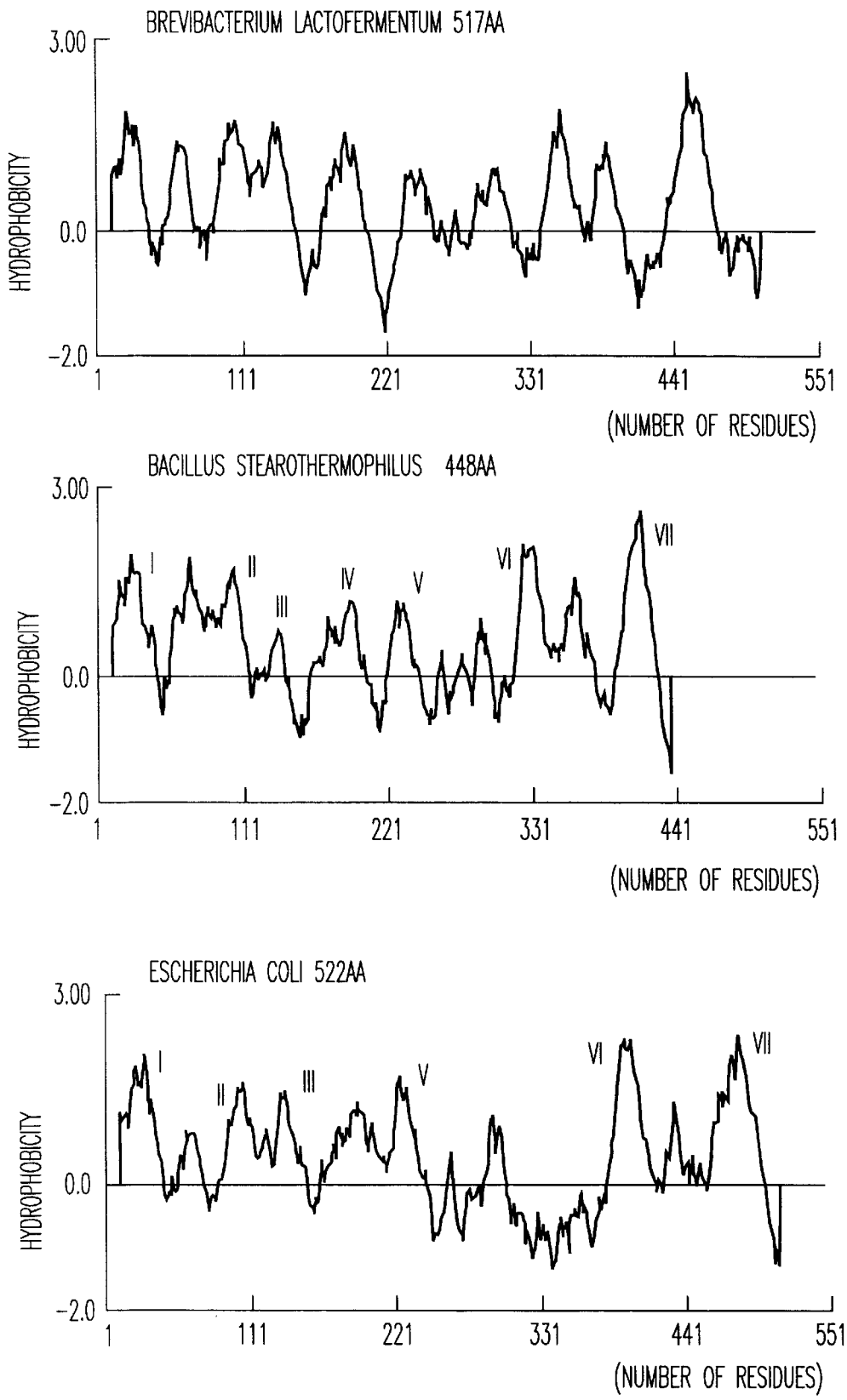
FIG. 1 represents the results of hydropathy analysis of subunits I of cytochrome bd type quinol oxidases of *Brevibacterium lactofermentum, Bacillus stearothermophilus* and *Escherichia coli*. The symbol "*" indicates an amino acid residue shared by the three oxidases.

The present invention will be explained in more detail hereinafter.

The DNA of the present invention can be obtained from *B. lactofermentum* chromosomal DNA based on partial amino acid sequences of cytochrome bd type quinol oxidase of *B. flavum*. Specifically, PCR is performed by using oligonucleotides synthesized based on the amino acid sequences as primers, and chromosomal DNA of *B. flavum* as template to obtain a partial sequence of cytochrome bd type quinol oxidase gene of *B. flavum*. Then, by screening a chromosomal DNA library of *B. lactofermentum* using the obtained partial sequence as a probe, a gene encoding cytochrome bd type quinol oxidase of *B. lactofermentum* can be obtained.

Chromosomal DNA of *B. flavum* and *B. lactofermentum* can be prepared by, for example, the method of Saito and Miura (*Biochem. Biophys. Acta.,* 72, 619, (1963)), and the method of K. S. Kirby (*Biochem. J.,* 64, 405 (1956)). A chromosome DNA library can be obtained by partially digesting chromosomal DNA with a suitable restriction enzyme, ligating each of the obtained DNA fragments to a vector DNA autonomously replicable in *Escherichia coli* cell to prepare a recombinant DNA, and introducing the DNA into *E. coli*. The vector is not particularly limited, so long as it is a vector usually used for genetic cloning, and plasmid vectors such as pUC19, pUC18, pUC118, and puC119, phage vectors such as lambda phage DNA and the like can be used.

The primer used for the PCR may be, for example, an oligonucleotide having a nucleotide sequence shown in SEQ ID NO: 7 or SEQ ID NO: 8. In order to confirm that an obtained PCR product has a desired sequence, it can be confirmed that it contains a sequence corresponding to the primer by nucleotide sequencing, or confirming that the amino acid sequence deduced from the nucleotide sequence contains a partial amino acid sequence of cytochrome bd type quinol oxidase of *B. flavum.*

The screening of a chromosome DNA library of *B. lactofermentum* utilizing the DNA fragment obtained in the PCR as a probe can be performed by colony hybridization when plasmid vectors are used for the preparation of the library, or plaque hybridization when phage vectors are used for the preparation of the library. A hybridization positive clone can be confirmed to contain a purpose cytochrome bd type quinol oxidase gene by nucleotide sequencing of DNA prepared from the clone. It is also possible to preliminarily perform Southern analysis for a hybridization positive clone by using the probe.

A nucleotide sequence of cytochrome bd type quinol oxidase gene of *B. lactofermentum* ATCC 13869 strain obtained in the working example in such a manner as described above is shown in SEQ ID NO: 1. Expected coding regions and amino acid sequences of proteins encoded thereby are shown in SEQ ID NOS: 1–4. Estimation of coding regions and operon structure and analysis of homology to cytochrome bd type quinol oxidases of *Bacillus stearothermophilus* K1041 and *Escherichia coli* were performed by using GENETYX-Homology Version 2.2.2 (Software Development Co., Ltd.).

The cytochrome bd type quinol oxidase gene contains two open reading frames (cydA and cydB reading from the 5' end), and they encode subunit I of cytochrome bd type quinol oxidase (also referred to as merely "subunit I" hereinafter) and subunit II of the same (also referred to as merely "subunit II" hereinafter), respectively. It was estimated that cydA and cydB comprised 1551 bp and 1023 bp respectively, the subunit I consisted of 517 amino acid residues and the subunit II consisted of 341 amino acid residues. A promoter-like sequence was present upstream of cydA, an SD-like sequence was present upstream of each of cydA and cydB, and a terminator-like sequence was present downstream of cydB. Therefore, it was considered that cydA and cydB formed a cyd operon.

While the codon of the N-terminal amino acid residue of the subunit I is indicated as GTG, and the corresponding amino acid as Val in Sequence Listing, it is actually Met. This is considered to be caused because GTG is recognized as an initiation methionine. Such cases have been reported elsewhere.

FIGS. 1 and 2 represent the results of hydropathy analysis performed for comparison of structures of the cytochrome bd type quinol oxidase of the present invention and subunits I of *Bacillus stearothermophilus* and *E. coli,* and alignment of the amino acid sequences. The indications I–VII represent transmembrane helix regions, and therefore it was confirmed that there were at least seven transmembrane helices. It can be understood from the patterns shown in the graphs that they resemble each other. Further, a region containing a quinol binding site called Q loop was present between V and VI of the subunit I of *E. coli,* whereas there was no region exhibiting homology with the latter half portion of the Q loop in *B. lactofermentum* like *B. stearothermophilus* cydA, and hence the Q loop region was shortened. Considering this point, it is expected that cytochrome bd type quinol oxidase of *B. lactofermentum* has a structure more similar to that of cytochrome bd type quinol oxidase of *B. stearothermophilus* rather than that of *E. coli.* The comparison of amino acid sequences of the subunit I showed that *B. lactofermentum* has about 24.7% homology to *B. stearothermophilus* and, about 38.6% to *E. coli,* and it was considered that, as for the subunit I as a whole, cytochrome bd type quinol oxidase of *B. lactofermentum* has a structure more similar to cytochrome bd type quinol oxidase of *E. coli* rather than that of *B. stearothermophilus.*

There have been reported H19, H186, and M393 for *E. coli* cydA, and H21, H184, and M326 for *B. stearothermophilus* cydA as functionally important residues in view of being a ligand of hem b558. These amino acids are conserved also in cydA of *B. lactofermentum* as H18, H185, and M350.

FIG. 3 represents alignment of amino acid sequences of the three kinds of bacterial subunits II. As for the subunit II, *B. lactofermentum* showed about 25.9% homology to *B. stearothermophilus,* and about 34.8% to *E. coli.*

The DNA of the present invention is a DNA encoding the subunit I, which is encoded by the nucleotide sequence shown in SEQ ID NO: 2, the subunit II, which is encoded by the nucleotide sequence shown in SEQ ID NO: 4, or cytochrome bd type quinol oxidase protein containing these subunit I and subunit II. The subunit I, subunit II or cytochrome bd type quinol oxidase protein can be produced by introducing such a DNA into a suitable host cell, and culturing the obtained transformant so that the DNA should be expressed. A DNA having a nucleotide sequence comprising nucleotides of the nucleotide numbers 933–2483 in the nucleotide sequence shown in SEQ ID NO: 1 can be mentioned as a DNA encoding the subunit I, a DNA having a nucleotide sequence comprising nucleotides of the nucleotide numbers 2476–3498 as a DNA encoding the subunit II, and a DNA having a nucleotide sequence comprising nucleotides of the nucleotide numbers 933–3498 as a DNA encoding the both.

The produced cytochrome bd type quinol oxidase protein or a subunit thereof can be collected and purified from culture by a method commonly used for the purification of proteins such as salting out, solvent precipitation, gel filtration chromatography, and ion exchange chromatography.

The DNA of the present invention encoding the subunit I may be either one encoding a polypeptide having an amino acid sequence shown in SEQ ID NO: 2 comprising substitution, deletion, insertion, addition or inversion of one or a plurality of amino acid residues in the amino acid sequence, or a polypeptide that can constitute a protein exhibiting cytochrome bd type quinol oxidase activity together with the subunit II.

The DNA of the present invention encoding the subunit II may be either one encoding a polypeptide having an amino acid sequence shown in SEQ ID NO: 4 comprising substitution, deletion, insertion, addition or inversion of one or a plurality of amino acid residues in the amino acid sequence, or a polypeptide that can constitute a protein exhibiting cytochrome bd type quinol oxidase activity together with the subunit I.

Further, a DNA encoding a cytochrome bd type quinol oxidase which contains mutations in the subunit I, the subunit II or the both is also included in the DNA of the present invention.

The term "a plurality of amino acid residues" preferably means 1–40, more preferably 1–10 amino acid residues.

DNA, which codes for the substantially same protein as subunit I and/or the subunit II as described above, is obtained, for example, by modifying the nucleotide sequence, for example, by means of the site-directed mutagenesis method so that one or more amino acid residues at a specified site involve substitution, deletion, insertion, addition, or inversion. DNA modified as described above may be obtained by the conventionally known mutation treatment. The mutation treatment includes a method for treating DNA coding for subunit I and/of the subunit II in vitro, for example, with hydroxylamine, and a method for treating a microorganism, for example, a bacterium belonging to the genus Escherichia harboring DNA coding for subunit I and/of the subunit II with ultraviolet irradiation or a mutating agent such as N-methyl-N'-nitro-N-nitrosoguanidine (NTG) and nitrous acid usually used for the mutation treatment.

The substitution, deletion, insertion, addition, or inversion of nucleotide as described above also includes mutation (mutant or variant) which naturally occurs, for example, on the basis of the individual difference or the difference in species or genus of coryneform bacteria which harbors cytochrome bd type quinol oxidase.

The DNA, which codes for substantially the same protein as subunit I and/of the subunit II, is obtained by expressing DNA having mutation as described above in an appropriate cell, and investigating an activity of an expressed product. The DNA, which codes for substantially the same protein as subunit I and/of the subunit II, is also obtained by isolating DNA which is hybridizable with DNA having, for example, a nucleotide sequence corresponding to nucleotide numbers of 933 to 2483 of the nucleotide sequence depicted in SEQ ID NO: 1 and/or a nucleotide sequence corresponding to nucleotide numbers of 2476 to 3498 of the nucleotide sequence depicted in SEQ ID NO: 3 in Sequence Listing under a stringent condition, and which codes for a protein having the activity of subunit I and/or subunit II, from DNA coding for subunit I and/or subunit II having mutation or from a cell harboring it.

The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 50% are hybridized with each other, and DNA's having homology lower than the above are not hybridized with each other. Alternatively, the stringent condition is exemplified by a condition under which DNA's are hybridized with each other at a salt concentration corresponding to an ordinary condition of washing in Southern hybridization, i.e., 60° C., 1×SCC, 0.1% SDS, preferably 0.1×SSC, 0.1% SDS.

The gene, which is hybridizable under the condition as described above, includes those having a stop codon generated within a coding region of the gene, and those having no activity due to mutation of active center. However, such inconveniences can be easily removed by ligating the gene with a commercially available activity expression vector, and investigating cytochrome bd type quinol oxidase activity.

The host for the expression of the DNA of the present invention include, for example, various kinds of bacteria including E. coli, coryneform bacteria such as B. lactofermentum and B. flavum, eucaryotic cells such as Saccharomyces cerevisiae and the like. In order to introduce the DNA of the present invention into a host such as those mentioned above, the host cell can be transformed with a recombinant vector which is obtained by inserting the DNA of the present invention into a vector selected depending on the kind of the host in which the expression is to be obtained. Those procedures can be performed by using methods of genetic recombination well known to those skilled in the art.

The DNA of the present invention and cytochrome bd type quinol oxidase or the subunits thereof encoded thereby are considered to be useful for elucidating the electron transport system of coryneform bacteria. The DNA of the present invention is also expected to be utilized for breeding of coryneform bacteria producing useful substances with high energy efficiency.

BEST MODE FOR CARRYING OUT THE INVENTION

The present invention will be specifically explained with reference to the following examples.

<1> Purification of Cytochrome bd Type Quinol Oxidase of Brevibacterium flavum

Bacterial cells (about 120 g wet weight) of B. flavum ATCC 14067 strain that had been cultivated by the end of the stationary phase were suspended in 200 ml of a buffer (0.5% NaCl, 10 mM sodium phosphate, pH 7.4), and immediately disrupted by stirring at a high speed by means of a bead beater (Biospec) in the presence of 0.5 mM of glass particles. After this suspension of disrupted cells was centrifuged at 5,000 rpm for 10 minutes to remove undisrupted bacterial cells, the supernatant was subjected to centrifugation at 15,000 rpm for 10 minutes and the resulting supernatant was further subjected to centrifugation at 15,000 rpm for 30 minutes. The precipitates obtained in the both centrifugations were combined, and suspended in the same buffer as mentioned above to obtain a membrane preparation.

The above membrane preparation (5 mg/ml, 0.5% NaCl, 10 mM sodium phosphate, pH 7.4) was homogenized by a Teflon homogenizer, and centrifuged at 40,000 rpm for 20 minutes, and precipitates were collected. The precipitates were added with 1.5% sodium cholate, 0.5% sodium deoxycholate, 0.1% NaCl, and 10 mM sodium phosphate (pH 7.4), then homogenized and centrifuged at 40,000 rpm for 20 minutes to collect the precipitates. The precipitates were further added with 10 mM sodium phosphate (pH 7.4), homogenized, and centrifuged at 40,000 rpm for 20 minutes to collect the precipitates.

The membrane preparation washed with cholic acid as described above was suspended in a buffer containing surface active agents, n-nonanoyl-N-methylglucamide (MEGA-9) and decanoyl-N-methylglucamide (MEGA-10) each at 1%. This suspension was homogenized on ice, sonicated, and centrifuged at 40,000 rpm for 20 minutes to obtain a supernatant.

The above supernatant obtained by the centrifugation was adsorbed on a hydroxyapatite column equilibrated with 1% MEGA-9, 1% MEGA-10, 10% glycerol, and 10 mM sodium phosphate (pH 7.4), and fractionated by elution with a concentration of sodium phosphate increased stepwise (0, 50, 150, 250, and 400 mM). Cytochromes in the fractions were detected by reduced minus oxidized difference spectrum. As a result, cytochromes c and b were detected in the fraction eluted at 50 mM of sodium phosphate, cytochromes c, b and a in the fraction eluted at 150 mM, and cytochromes b and d in the fraction eluted at 250 mM.

The fraction eluted at a sodium phosphate concentration of 250 mM was dialyzed against 10% glycerol and 10 mM sodium phosphate (pH 7.4), then adsorbed on a DEAE-Toyopearl (Tohso) column equilibrated with the same buffer, and fractionated by elution with a concentration of NaCl increases stepwise (0, 80, 100, 120, 140, and 300 mM). Cytochromes in the fractions were detected by reduced minus oxidized difference spectrum. As a result, cytochromes b and d were detected in the fraction eluted at a NaCl concentration of 120 mM. This fraction was used as cytochrome bd type quinol oxidase enzyme preparation.

The above enzyme preparation was subjected to SDS-polyacrylamide gel electrophoresis using 13.5% gel, and blotted on a PVDF membrane. Portions of the membrane corresponding to the subunit I and the subunit II were subjected to amino acid sequence analysis to determine the N-terminal amino acid sequence. The amino acid sequences are shown in SEQ ID NO: 5 (subunit I) and SEQ ID NO: 6 (subunit II), respectively.

<2> Isolation of Cytochrome bd Yype Quinol Oxidase Gene of *Brevibacterium lactofermentum*

Screening of a chromosome DNA library of *B. lactofermentum* for clone containing cytochrome bd type quinol oxidase gene was performed by colony hybridization.

Two kinds of oligonucleotides were synthesized based on the above partial amino acid sequences of cytochrome bd type quinol oxidase *B. flavum*. One was prepared based on the N-terminal amino acid sequence of the subunit I of cytochrome bd type quinol oxidase (bbd1: SEQ ID NO: 7), and the other was prepared based on the N-terminal amino acid sequence of the subunit II (bbd2: SEQ ID NO: 8).

PCR was performed by using the above primers bbd1 and bbd2 and chromosome DNA of the strain ATCC 14067 as template. As for the reaction condition, after denaturation at 94° C. for one minute, a cycle comprising denaturation at 95° C. for 45 seconds, annealing at 50° C. for 60 seconds, and chain extension reaction at 62° C. for 90 seconds was repeated for 35 cycles. As a result, fragments of about 1500 bp, 800 bp, and 100 bp were provided. Based on the molecular weight 56.4 kD of the subunit I estimated from the purified protein, and the reported molecular weights of subunits I of cytochrome bd type quinol oxidases of other bacteria, the fragment of about 1500 bp was considered to be the desired PCR product. Therefore, the PCR product was electrophoresed on 2% agarose gel, and a portion of about 1.5 kbp fragment was excised from the gel to extract the DNA.

This DNA fragment was blunt-ended by using DNA Blunting Kit (Takara Shuzo), and ligated to pUC118 vector digested with SmaI and treated with alkaline phosphatase by using DNA ligation Kit Ver. 2 (Takara Shuzo). *E. coli* XL-1 Blue strain was transformed with the obtained recombinant primer.

Plasmid was prepared from the obtained transformant, and the inserted nucleotide sequence was determined. The nucleotide sequencing was performed by using Fluorescein Labeled Primer M4 (Takara Shuzo, SEQ ID NO: 9) as the forward primer, the Fluorescein Labeled Primer RV-MF (Takara Shuzo, SEQ ID NO: 10) as the reverse primer according to the protocol of Thermo Sequence fluorescent labelled primer cycle sequencing kit (Amersham Life Science). As a result, it was confirmed that the cytochrome bd type quinol oxidase gene was contained in the plasmid based on the homology with the primer. This partial clone was designated BD1.

This BD1 was amplified by PCR using the aforementioned primers M4 and RV-M, and a probe labeled with DIG (digoxigenin) was prepared by using DIG DNA Labeling Kit (Boehringer Mannheim).

Chromosomal DNA library of *B. lactofermentum* was screened by using the aforementioned probe. The library was obtained by partially digesting chromosomal DNA of *B. lactofermentum* ATCC 13869 with Sau3A1, inserting the product into BamHI site of pUC18, and transforming *E. coli* XL-1 Blue with the obtained recombinant plasmid. Colony hybridization was performed for the colonies of transformants by using the probe labeled with DIG mentioned above. The detection of the probe was performed by using DIG Detection Kit (Boehringer Mannheim) which utilized anti-DIG antibodies labeled with alkaline phosphatase.

Plasmid was prepared from hybridization positive colonies, digested with EcoRI and PstI, and subjected to Southern blotting using BD1 as a probe. As a result, two positive clones were obtained. Inserted fragments of these positive clones were designated BD21 and BD31, respectively. BD21 comprised about 3.8 kbp, and BD31 comprised about 9.0 kbp. These clones were subcloned and their nucleotide sequences were determined. The results are shown in SEQ ID NO: 1. Expected coding regions and amino acid sequences of the proteins encoded thereby are shown in SEQ ID NOS: 1–4.

What is claimed is:

1. A DNA fragment encoding a polypeptide defined in the following (A) or (B);
   (A) a polypeptide which has an amino acid sequence shown in SEQ ID NO: 2,
   (B) a polypeptide which has an amino acid sequence shown in SEQ ID NO: 2 comprising substitution, deletion, insertion, or addition of one to forty amino acid residues in the amino acid sequence, and can constitute a protein exhibiting cytochrome bd type quinol oxidase activity together with a subunit II of cytochrome bd type quinol oxidase having an amino acid sequence shown in SEQ ID NO: 4.

2. A DNA fragment encoding a polypeptide defined in the following (C) or (D);
   (C) a polypeptide which has an amino acid sequence shown in SEQ ID NO: 4,
   (D) a polypeptide which has an amino acid sequence shown in SEQ ID NO: 4 comprising substitution, deletion, insertion, or addition of one to forty of amino acid residues in the amino acid sequence, and can constitute a protein exhibiting cytochrome bd type quinol oxidase activity together with a subunit I of cytochrome bd type quinol oxidase having an amino acid sequence shown in SEQ ID NO: 2.

3. A DNA fragment encoding a polypeptide defined in the following (A) or (B), and a polypeptide defined in the following (C) or (D);
   (A) a polypeptide which has an amino acid sequence shown in SEQ ID NO: 2,
   (B) a polypeptide which has an amino acid sequence shown in SEQ ID NO: 2 comprising substitution, deletion, insertion, or addition of one to forty of amino acid residues in the amino acid sequence, and can constitute a protein exhibiting cytochrome bd type quinol oxidase activity together with a subunit II of cytochrome bd type quinol oxidase having an amino acid sequence shown in SEQ ID NO: 4,
   (C) a polypeptide which has an amino acid sequence shown in SEQ ID NO: 4,
   (D) a polypeptide which has an amino acid sequence shown in SEQ ID NO: 4 comprising substitution, deletion, insertion, or addition of one to forty amino acid residues in the amino acid sequence, and can constitute a protein exhibiting cytochrome bd type quinol oxidase activity together with a subunit I of cytochrome bd type quinol oxidase having an amino acid sequence shown in SEQ ID NO: 2.

4. The DNA according to claim 1, which is a DNA defined in the following (a) or (b):
   (a) a DNA having a nucleotide sequence corresponding to nucleotide numbers 933 to 2483 in the nucleotide sequence depicted in SEQ ID NO: 1; or
   (b) a DNA which is hybridizable with the nucleotide sequence of above (a) under stringent conditions of 1×SSC, 0.1% SDS at 60° C., and which encodes a polypeptide which can constitute a protein exhibiting cytochrome bd type quinol oxidase activity together with a subunit II of cytochrome bd type quinol oxidase having an amino acid sequence shown in SEQ ID NO: 4.

5. The DNA according to claim 2, which is a DNA defined in the following (c) or (d):
   (c) a DNA having a nucleotide sequence corresponding to nucleotide numbers 2476 to 3498 in the nucleotide sequence depicted in SEQ ID NO: 3; or
   (d) a DNA which is hybridizable with the nucleotide sequence of above (c) under stringent conditions of 1×SSC, 0.1% SDS at 60° C., and which encodes a polypeptide which can constitute a protein exhibiting cytochrome bd type quinol oxidase activity together with a subunit I of cytochrome bd type quinol oxidase having an amino acid sequence shown in SEQ ID NO: 2.

6. The DNA according to claim 3, which comprises a DNA defined in the following (a) or (b), and a DNA defined in the following (c) or (d):
   (a) a DNA having a nucleotide sequence corresponding to nucleotide numbers 933 to 2483 in the nucleotide sequence depicted in SEQ ID NO: 1; or
   (b) a DNA which is hybridizable with the nucleotide sequence of above (a) under stringent conditions of 1×SSC, 0.1% SDS at 60° C., and which encodes a polypeptide which can constitute a protein exhibiting cytochrome bd type quinol oxidase activity together with a subunit II of cytochrome bd type quinol oxidase having an amino acid sequence shown in SEQ ID NO: 4; and
   (c) a DNA having a nucleotide sequence corresponding to nucleotide numbers 2476 to 3498 in the nucleotide sequence depicted in SEQ ID NO: 3; or
   (d) a DNA which is hybridizable with the nucleotide sequence of above (c) under stringent condition conditions of 1×SSC, 0.1% SDS at 60° C., and which encodes a polypeptide which can constitute a protein exhibiting cytochrome bd type quinol oxidase activity together with a subunit I of cytochrome bd type quinol oxidase having an amino acid sequence shown in SEQ ID NO: 2.

7. The DNA fragment of claim 1, which has a nucleotide sequence comprising nucleotides of the nucleotide numbers 933 to 2483 in the nucleotide sequence shown in SEQ ID NO: 1.

8. The DNA fragment of claim 2, which has a nucleotide sequence comprising nucleotides of the nucleotide numbers 2476 to 3498 in the nucleotide sequence shown in SEQ ID NO: 1.

9. The DNA fragment of claim 3, which has a nucleotide sequence comprising nucleotides of the nucleotide numbers 933 to 3498 in the nucleotide sequence shown in SEQ ID NO: 1.

10. The DNA fragment of claim 4, which is (a).
11. The DNA fragment of claim 4, which is (b).
12. The DNA fragment of claim 5, which is (c).
13. The DNA fragment of claim 5, which is (d).

* * * * *

UNITED STATES PATENT AND TRADEMARK OFFICE
CERTIFICATE OF CORRECTION

PATENT NO.    : 6,156,886
DATED         : December 5, 2000
INVENTOR(S)   : Nobuhito Sone It is certified that error appears in the above-identified patent and that said Letters Patent is hereby corrected as shown below:

Column 27,
Lines 33-44, "1. DNA fragment encoding a polypeptide defined in the following (A) or (B);
(A) a polypeptide which has an amino acid sequence shown in SEQ ID NO: 2,
(B) a polypeptide which has an amino acid sequence shown in SEQ ID NO: 2 comprising substitution, deletion, insertion, or addition of one to forty amino acid residues in the amino acid sequence, and can constitute a protein exhibiting cytochrome bd type quinol oxidase activity together with a subunit II of cytochrome bd type quinol oxidase having an amino acid sequence shown in SEQ ID NO: 4." should read -- 1. A DNA fragment encoding a polypeptide which has an amino acid sequence shown in SEQ ID NO: 2 --.
Lines 45-56, " 2. A DNA fragment encoding a polypeptide defined in the following (C) or (D),
(C) a polypeptide which has an amino acid sequence shown in SEQ ID NO: 4,
(D) a polypeptide which has an amino acid sequence shown in SEQ ID NO: 4 comprising substitution, deletion, insertion, or addition of one to forty of amino acid residues in the amino acid sequence, and can constitute a protein exhibiting cytochrome bd type quinol oxidase activity together with a subunit I of cytochrome bd type quinol oxidase having an amino acid sequence shown in SEQ ID NO: 2." should read -- 2. A DNA fragment encoding a polypeptide which has an amino acid sequence shown in SEQ ID NO: 4. --.

Column 27, lines 57-68 through Column 28, lines 31-42,
"3. A DNA fragment encoding a polypeptide defined in  the following (A) or (B), and a polypeptide defined in the following (C) or (D);
(A) a polypeptide which has an amino acid sequence shown in SEQ ID NO: 2, and
(B) a polypeptide which has an amino acid sequence shown in SEQ ID NO: 2 comprising substitution, deletion, or addition of one to forty amino acid residues in the amino acid sequence, and can constitute a protein exhibiting cytochrome bd type quinol oxidase activity together with a subunit II of cytochrome bd type quinol oxidase having an amino acid sequence shown in SEQ ID NO: 4,
(C) a polypeptide which has an amino :acid sequence shown in SEQ ID NO: 4,
(D) a polypeptide which has an amino acid sequence shown in SEQ ID NO: 4 comprising substitution, deletion, insertion, or addition of one to forty of amino acid residues in the amino acid sequence, and can constitute a protein exhibiting cytochrome bd type quinol oxidase activity together with a subunit I of cytochrome bd type quinol oxidase having an amino acid sequence shown in SEQ ID NO: 2." should read -- 3. A DNA fragment encoding a polypeptide which has an amino acid sequence shown in SEQ ID NO: 2 and a polypeptide which has an amino acid sequence shown in SEQ ID NO: 4. --.

UNITED STATES PATENT AND TRADEMARK OFFICE
CERTIFICATE OF CORRECTION

| | | |
|---|---|---|
| PATENT NO. | : 6,156,886 | |
| DATED | : December 5, 2000 | |
| INVENTOR(S) | : Nobuhito Sone | |

It is certified that error appears in the above-identified patent and that said Letters Patent is hereby corrected as shown below:

Column 28,
Lines 43-54, "4. The DNA according to claim 1, which is a DNA defined in the following (a) or (b):
(a) DNA having a nucleotide sequence corresponding to nucleotide numbers 933 to 2483 in the nucleotide sequence depicted in SEQ ID NO: 1; or
(b) a DNA which is hybridizable with the nucleotide sequence of above (a) under stringent conditions of 1xSSC, 0.1% SDS at 60° C., and which encodes a polypeptide which can constitute a protein exhibiting cytochrome bd type quinol oxidase activity together with a subunit II of cytochrome bd type quinol oxidase having an amino acid sequence shown in SEQ ID NO: 4." should read -- 4. A DNA, which is a DNA defined in the following (a) or (b):
(a) DNA having a nucleotide sequence corresponding to nucleotide numbers 933 to 2483 in the nucleotide sequence depicted in SEQ ID NO: 1; or
(b) a DNA which is hybridizable with the nucleotide sequence of above (a) under stringent conditions of IxSSC, 0.1% SDS at 60° C., and which encodes a polypeptide which can constitute a protein exhibiting cytochrome bd type quinol oxidase activity together with a subunit II of cytochrome bd type quinol oxidase having an amino acid sequence shown in SEQ ID NO: 4.--
Lines 55-57, "5. The DNA according to claim 2, which is a DNA defined in the following (c) or (d):
(c) a DNA having a nucleotide sequence corresponding to nucleotide numbers 2476 to 3498 in the nucleotide sequence depicted in SEQ ID NO: 3; or
(d) a DNA which is hybridizable with the nucleotide sequence of above (c) under stringent conditions of 1xSSC, 0.1% SDS at 60° C., and which encodes a polypeptide which can constitute a protein exhibiting cytochrome bd type quinol oxidase activity together with a subunit I of cytochrome bd type quinol oxidase having an amino acid sequence shown in SEQ ID NO: 2." should read -- 5. A DNA, which is a DNA defined in the following (c) or (d):
(c) a DNA having a nucleotide sequence corresponding to nucleotide numbers 2476 to 3498 in the nucleotide sequence depicted in SEQ ID NO: 3; or
(d) a DNA which is hybridizable with the nucleotide sequence of above (c) under stringent conditions of 1xSSC, 0.1% SDS at 60° C., and which encodes a polypeptide which can constitute a protein exhibiting cytochrome bd type quinol oxidase activity together with a subunit I of cytochrome bd type quinol oxidase having an amino acid sequence shown in SEQ ID NO: 2.--

UNITED STATES PATENT AND TRADEMARK OFFICE
CERTIFICATE OF CORRECTION

PATENT NO. : 6,156,886
DATED : December 5, 2000
INVENTOR(S) : Nobuhito Sone

It is certified that error appears in the above-identified patent and that said Letters Patent is hereby corrected as shown below:

<u>Column 29, lines 1-23 through Column 30, lines 1-4,</u>
"6. The DNA according to claim 3, which comprises a DNA defined in the following (a) or (b), and a DNA defined in the following (c) or (d):
(a) a DNA having a nucleotide sequence corresponding to nucleotide numbers 933 to 2483 in the nucleotide sequence depicted in SEQ ID NO: 1; or
(b) a DNA which is hybridizable with the nucleotide sequence of above (a) under stringent conditions of 1xSSC, 0.1% SDS at 60° C., and which encodes a polypeptie which can constitute a protein exhibiting cytochirome bd type quinol oxidase activity together with a subunit II of cytochrome bd type quinol oxidase having an amino acid sequence shown in SEQ ID NO: 4; and
(c) a DNA having a nucleotide sequence corresponding to nucleotide numbers 2476 to 3498 in the nucleotide sequence depicted in SEQ ID NO. 3; or
(d) a DNA which is hybridizable with the nucleotide sequence of above (c) under stringent condition conditions of 1xSSC, 0.1% SDS at 60° C., and which encodes a polypeptide which can constitute a protein exhibiting cytochrome bd type quinol exidase activity together with a subunit I of cytochrome bd type quinol oxidase having an amino acid sequence shown in SEQ ID NO: 2." should read -- 6. A DNA, which comprises a DNA defined in the following (a) or (b), and a DNA defined in the following (c) or (d):
(a) a DNA having a nucleotide sequence corresponding to nucleotide numbers 933 to 2483 in the nucleotide sequence depicted in SEQ ID NO: 1; or
(b) a DNA which is hybridizable with the nucleotide sequence of above (a) under stringent conditions of 1xSSC. 0.1% SDS at 60° C.. and which encodes a polypeptide which can constitute a protein exhibiting cytochrome bd type quinol oxidase activity together with a subunit II of cytochrome bd type quinol oxidase having an amino acid sequence shown in SEQ ID NO: 4; and
(c) a DNA having a nucleotide sequence corresponding to nucleotide numbers 2476 to 3498 in the nucleotide sequence depicted in SEQ ID NO: 3; or
(d) a DNA which is hybridizable with the nucleotide sequence of above (c) under stringent conditions encodes a polypeptide which can constitute a protein exhibiting

UNITED STATES PATENT AND TRADEMARK OFFICE
CERTIFICATE OF CORRECTION

PATENT NO. : 6,156,886
DATED : December 5, 2000
INVENTOR(S) : Nobuhito Sone

It is certified that error appears in the above-identified patent and that said Letters Patent is hereby corrected as shown below:

Column 29, lines 1-23 through Column 30, lines 1-4 (cont'd),
cytochrome bd type quinol oxidase activity together with a
subunit I of cytochrome bd type quinol oxidase having an-amino acid sequence shown in
SEQ ID NO: 2.--

Signed and Sealed this

Thirteenth Day of July, 2004

JON W. DUDAS
*Acting Director of the United States Patent and Trademark Office*